United States Patent [19]

Tomioka et al.

[11] Patent Number: 5,283,324
[45] Date of Patent: Feb. 1, 1994

[54] PROCESS FOR PREPARING RADIATION SENSITIVE COMPOUND AND POSITIVE RESIST COMPOSITION

[75] Inventors: Jun Tomioka, Takarazuka; Koji Kuwana, Fujiidera; Hirotoshi Nakanishi, Osaka; Hiroshi Takagaki, Higashiosaka; Yasunori Doi, Takatsuki; Yasunori Uetani, Toyonaka; Ryotaro Hanawa, Ibaraki, all of Japan

[73] Assignee: Sumitomo Chemical Company, Limited, Osaka, Japan

[21] Appl. No.: 869,968

[22] Filed: Apr. 17, 1992

[30] Foreign Application Priority Data

Apr. 17, 1991 [JP] Japan .................................. 3-085147
Jul. 18, 1991 [JP] Japan .................................. 3-178184

[51] Int. Cl.$^5$ .................... C07C 303/28; G03F 7/022
[52] U.S. Cl. .................................. 534/557; 430/165; 430/191; 430/192; 430/193
[58] Field of Search ............................ 534/557

[56] References Cited

U.S. PATENT DOCUMENTS

| | | | |
|---|---|---|---|
| 3,050,389 | 8/1962 | Sus et al. | 534/557 X |
| 3,102,809 | 9/1963 | Endermann et al. | 534/557 X |
| 4,719,167 | 1/1988 | Miura et al. | 534/557 X |
| 4,992,596 | 2/1991 | Jefferies, III et al. | 534/557 X |
| 5,019,478 | 5/1991 | Toukhy et al. | 430/165 |
| 5,080,997 | 1/1992 | Hioki et al. | 430/192 X |

FOREIGN PATENT DOCUMENTS

| | | |
|---|---|---|
| 0372504 | 6/1989 | European Pat. Off. |
| 0346808 | 12/1989 | European Pat. Off. |
| 0363978 | 4/1990 | European Pat. Off. |
| 9007538 | 4/1990 | World Int. Prop. O. |

*Primary Examiner*—Mary C. Lee
*Assistant Examiner*—Fiona T. Powers
*Attorney, Agent, or Firm*—Birch, Stewart, Kolasch & Birch

[57] ABSTRACT

A radiation sensitive compound prepared by reacting a phenol compound with a quinone diazide sulfonyl halide in a mixture of a solvent having a relative dielectric constant of not larger than 10 and a solvent having a relative dielectric constant of at least 15, which compound is less colored and gives a positive resist composition having a good resolution.

11 Claims, No Drawings

PROCESS FOR PREPARING RADIATION SENSITIVE COMPOUND AND POSITIVE RESIST COMPOSITION

BACKGROUND OF THE INVENTION

1. Field of the Invention

The present invention relates to a process for preparing a radiation sensitive compound and a positive resist composition comprising said radiation sensitive compound which is produced by the process of the present invention.

2. Description of the Related Art

Hitherto, as a radiation sensitive component of a positive resist composition, a condensation product of a phenol compound and a quinone diazide sulfonyl halide has been used. When a hydroxyl group of the phenol compound is present near a group having a large steric hindrance or a ratio of the quinone diazide sulfonyl halide to the phenol compound is increased, a condensation reaction takes a long time in a solvent having a low relative dielectric constant. Depending on a kind of a sensitizer, a produced compound is precipitated in the solvent having the low relative dielectric constant. To solve such problems, it is proposed to increase an amount of a basic catalyst such as triethylamine. Though the increase of the catalyst amount shortens the reaction time and overcomes the precipitation problem, the radiation sensitive compound is severely colored so that resolution of a resist composition containing such compound is decreased.

SUMMARY OF THE INVENTION

One object of the present invention is to provide a process for preparing, in a greatly shortened reaction time, a radiation sensitive compound which is less colored.

Another object of the present invention is to provide a less colored radiation sensitive compound which is prepared by the process of the present invention and further a positive resist composition which comprises such less colored radiation sensitive compound and achieves good resolution.

According to a first aspect of the present invention, there is provided a process for preparing a radiation sensitive compound which comprises reacting a phenol compound with a quinone diazide sulfonyl halide in a mixture of a solvent having a relative dielectric constant of not larger than 10 (hereinafter referred to as a "low relative dielectric constant solvent") and a solvent having a relative dielectric constant of at least 15 (hereinafter referred to as a "high relative dielectric constant solvent").

According to a second aspect of the present invention, there is provided a positive resist composition comprising the radiation sensitive compound and an alkali soluble resin.

DETAILED DESCRIPTION OF THE INVENTION

In the process of the present invention, the radiation sensitive compound is prepared by reacting the phenol compound with the quinone diazide sulfonyl compound in a mixture of the low relative dielectric constant solvent and the high relative dielectric constant solvent, crystallizing the reaction product, and washing and drying it. In particular, the phenol compound and the quinone diazide sulfonyl halide are completely dissolved in the mixed solvent, a basic catalyst is dropwise added to the solution and then the reaction solution is kept warming. After the completion of the reaction, a hydrochloride of the basic catalyst is removed by filtration. The reaction solution is then discharged in ion-exchanged water and stirred for several hours to precipitate the product. The precipitate mass is recovered by filtration to obtain a crystal, which is washed by, for example, rinsing or repulping. The obtained wet cake is dried by heating under reduced pressure to obtain the desired radiation sensitive compound.

Examples of the basic catalyst are amines such as triethylamine, inorganic alkali metal salts such as sodium hydrogen carbonate, and the like.

Examples of the low relative dielectric constant solvent are dioxane, tetrahydrofuran, dichloromethane, chloroform, and the like.

Examples of the high relative dielectric constant solvent are $\gamma$-butyrolactone, N-methyl-2-pyrolidone, acetone, N,N-dimethylformamide, furfural, nitrobenzene, sulforane and alcohols having a relative dielectric constant of at least 15 (e.g. methanol, ethanol, 1-propanol, 2-propanol, 1-butanol, 2-butanol, etc.). Among them, the alcohols, in particular methanol are preferred.

Among the mixed solvents, a mixture of a solvent having a relative dielectric constant of 5 or less and a solvent having a relative dielectric constant of at least 20, for example a mixture of the solvent having a relative dielectric constant of 5 or less and $\gamma$-butyrolactone or methanol, in particular a mixed solvent of dioxane and $\gamma$-butyrolactone or methanol is preferred.

An amount of the high relative dielectric constant solvent except for the alcohols is 50% by weight or less, preferably 20% by weight or less, based on the whole weight of the mixed solvent. The lower limit of the amount of the high relative dielectric constant solvent is larger than 0% by weight, preferably 1% by weight or more.

When the alcohol is used as a high relative dielectric constant solvent, an amount of the alcohol is preferably 1% by weight or less, particularly 0.1% by weight or less, based on the whole weight of the mixed solvent. The lower limit of the amount of the alcohol is the same as others.

Specific examples of the phenol compound are tetrahydroxybenzophenones (e.g. 2,3,3',4-tetrahydroxybenzophenone, 2,3,4,4'-tetrahydroxybenzophenone, 2,2',4,4'-tetrahydroxybenzophenone, 2,2',3,4-tetrahydroxybenzophenone, 2,2',3,4'-tetrahydroxybenzophenone, 2,2',5,5'-tetrahydroxybenzophenone, 2,3',4',5-tetrahydroxybenzophenone, 2,3',5,5'-tetrahydroxybenzophenone, etc.); pentahydroxybenzophenones (e.g. 2,2', 3,4,4'-pentahydroxybenzophenone, 2,2',3,4,5'-pentahydroxybenzophenone, 2,2',3,3',4-pentahydroxybenzophenone, 2,3,3',4,5'-pentahydroxybenzophenone, etc.); hexahydroxybenzophenones (e.g. 2,3,3',4,4',5'-hexahydroxybenzophenone, 2,2',3,3',4,5'-hexahydroxybenzophenone, etc.); alkyl gallates; oxyfravans of the formula (I):

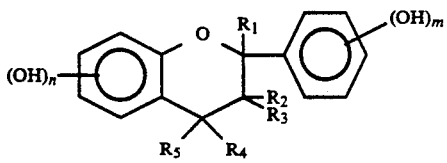

(I)

wherein n is a number of 0 to 3 and m is a number of 1 (one) to 4 provided that a sum of n and m is at least 1, $R_1$ to $R_5$ are independently a hydrogen atom, an alkyl group having preferably 1 to 4 carbon atoms, an alkenyl group having preferably 2 to 4 carbon atoms, a cycloalkyl group having preferably 5 to 7 carbon atoms or an aryl group such as a phenyl group, a naphthyl group, etc., or a pair of $R_1$ and $R_2$ and a pair of $R_4$ and $R_5$ independently forms a ring, provided that at least one of $R_4$ and $R_5$ is an alkyl group, an alkenyl group, a cycloalkyl group or an aryl group; and a phenol compound of the formula (I) disclosed in Japanese Patent Kokai Publication No. 269351/1990 and corresponding U.S. patent application Ser. No. 07/347,065 and EP-A-0 341 608).

Specific Examples of the quinone diazide sulfonyl halide are 1,2-benzoquinone diazide-4-sulfonyl chloride, 1,2-naphthoquinone diazide-4-sulfonyl chloride, 1,2-naphthoquinone diazide-5-sulfonyl chloride and the like.

The positive resist composition of the present invention contains the radiation sensitive compound which is prepared by the process of the present invention and an alkali soluble resin.

A novolak resin is preferably used as the alkali soluble resin. The novolak resin is prepared by an addition condensation reaction of a phenol with an aldehyde such as formaldehyde and the like. Specific examples of the phenol used as one of the raw materials for the novolak resin include phenol, cresol, xylenol, ethylphenol, trimethylphenol, propylphenol, butylphenol, dihydroxybenzene, naphthols, etc. These phenols may be used alone or in combination.

Among the phenols, cresols are preferably used. As cresol, m-cresol alone or a mixture of m-cresol and p-cresol can be used.

The aldehyde which undergoes the addition condensation reaction with the phenol can be used in the form of an aqueous solution of formaldehyde (formalin) or paraformaldehyde. In particular, 37% formalin which is commercially mass produced is suitably used.

The addition condensation reaction of the phenol with the aldehyde can be carried out according to a usual method. This reaction is carried out at a temperature of 60° to 120° C. for 2 to 30 hours. Organic acids, inorganic acids or divalent metal salts are used as catalysts. Specific examples of the catalyst are oxalic acid, hydrochloric acid, sulfuric acid, perchloric acid, p-toluenesulfonic acid, trichloroacetic acid, phosphoric acid, formic acid, zinc acetate, magnesium acetate, etc.

The reaction may be carried out in the presence or absence of a solvent.

The positive resist composition may be prepared by mixing and dissolving the above radiation sensitive compound and the alkali soluble resin in a solvent. A weight ratio of the alkali soluble resin to the radiation sensitive compound is preferably from 1:1 to 6:1. Preferably, the used solvent evaporates at a suitable drying rate to give a uniform and smooth coating film. Such solvent includes ethylcellosolve acetate, methylcellosolve acetate, ethylcellosolve, methylcellosolve, propylene glycol monomethyl ether acetate, butyl acetate, methyl isobutyl ketone, xylene and the like.

PREFERRED EMBODIMENTS OF THE INVENTION

The present invention will be illustrated by following Examples, which do not limit the scope of the present invention. In Examples, "parts" are by weight.

EXAMPLE 1

In a 500 ml four-necked flask, the compound of the following formula (1) (21.0 g), naphthoquinone-(1,2)-diazide-(2)-5-sulfonyl chloride (45.1 g) (a molar ratio of the compound (1) to the sulfonyl chloride = 1:2.4), dioxane (281 g) and γ-butyrolactone (50 g) were charged and stirred to achieve complete dissolution:

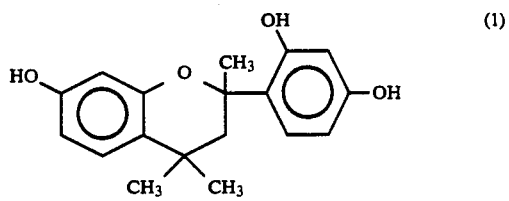

(1)

Then, triethylamine (18.7 g) was dropwise added over one hour while stirring and keeping the reaction temperature at 26° to 32° C., followed by stirring at 26° to 32° C. for 3 hours. Under the above conditions, the reaction time was 4 hours.

After the reaction, triethylamine hydrochloride was filtered off and a filtrate was discharged in ion-exchanged water. The precipitated product was recovered by filtration, washed with water and dried to obtain a radiation sensitive compound A.

EXAMPLE 2

In a 500 ml four-necked flask, the compound of the above formula (1) (21.0 g), naphthoquinone-(1,2)-diazide-(2)-5-sulfonyl chloride (48.9 g) (a molar ratio of the compound (1) to the sulfonyl chloride = 1:2.6), dioxane (350 g) and methanol (0.07 g) were charged and stirred to achieve complete dissolution. Then, triethylamine (21.2 g) was dropwise added over one hour while stirring and keeping the reaction temperature at 26° to 32° C., followed by stirring at 26° to 32° C. for 3 hours. Under the above conditions, the reaction time was 4 hours.

After the reaction, triethylamine hydrochloride was filtered off and a filtrate was discharged in ion-exchanged water. The precipitated product was recovered by filtration, washed with water and dried to obtain a radiation sensitive compound B.

COMPARATIVE EXAMPLE 1

In the same manner as in Example 1 except that dioxane (331 g) was used in place of the mixture of dioxane (281 g) and γ-butyrolactone (50 g), an amount of triethylamine was changed from 18.7 g to 23.8 g, and the stirring time after the addition of triethylamine was extended up to 16 hours, the reaction was carried out to obtain a radiation sensitive compound C. The reaction time was 17 hours under the above conditions.

COMPARATIVE EXAMPLE 2

In the same manner as in Example 2 except that dioxane (350 g) was used in place of the mixture of dioxane (350 g) and methanol (0.07 g), an amount of triethylamine was changed from 21.2 g to 23.0 g, and the stirring time after the addition of triethylamine was extended up to 24 hours, the reaction was carried out to obtain a radiation sensitive compound D. The reaction time was 25 hours under the above conditions.

EXAMPLES 3-4 AND COMPARATIVE EXAMPLES 3-4

A 5% solution of each of the radiation sensitive compounds A to D in ethylcellosolve acetate was prepared and stored at 23° C. for 10 days. Then, an absorbance at a wavelength of 700 nm was measured. The results are shown in Table 1

TABLE 1

| Example No. | Radiation sensitive compound | Absorbance |
| --- | --- | --- |
| 3 | A | 0.30 |
| Comp. 3 | C | 0.75 |
| 4 | B | 0.20 |
| Comp. 4 | D | 0.63 |

EXAMPLES 5-6 AND COMPARATIVE EXAMPLES 5-6

Each of the radiation sensitive compounds A to D and a novolak resin in a composition shown in Table 2 were dissolved in 44 parts of ethylcellosolve acetate. The resulting solution was filtered through a TEFLON (a trademark of DuPont) filter of 0.2 μm in pore size to obtain a resist solution. The resist solution was coated on a silicone wafer, which had been rinsed in a usual way, by means of a spinner so as to form a resist film of 1.27 μm in thickness. Subsequently, the silicon wafer was baked for 60 seconds on a hot plate kept at 90° C., and exposed to light having a wavelength of 365 nm (i line) while varying the exposure time stepwise by means of a reduction projection exposing apparatus (LD-5010i with NA of 0.40 manufactured by Hitachi). Thereafter, the silicon wafer was developed for one minute in a developing solution (SOPD manufactured by Sumitomo Chemical Co., Ltd.) to obtain a positive pattern.

A γ-value is expressed in terms of tanθ the angle θ of which is obtained by plotting a standardized film thickness (=the retained film thickness/ the original film thickness) against a logarithm of the exposure amount and calculating the inclination of the plotted line.

A resolution is defined as a minimum size of a line-and-space pattern at which the pattern is separated without film thickness decrease at an exposure amount at which a line width ratio (L/S) is one in the line-and-space pattern of 0.6 μm.

The results are shown in Table 2.

TABLE 2

| | Resist composition | | | |
| --- | --- | --- | --- | --- |
| Example No. | Novolak[1] resin | Radiation sensitive compound | γ-Value | Resolution (μm) |
| 5 | 15 parts | A: 4 parts | 4.2 | 0.50 |
| Comp. 5 | 15 parts | C: 4 parts | 3.6 | 0.55 |
| 6 | 15 parts | B: 4 parts | 4.5 | 0.50 |
| Comp. 6 | 15 parts | D: 4 parts | 3.7 | 0.55 |

Note:
[1] A novolak resin which is prepared by reacting a cresol mixture (a molar ratio of m-isomer to p-isomer = 6:4) with formalin (a molar ratio of the cresols to formalin = 1:0.8) in the presence of oxalic acid as a catalyst under reflux and has a weight average molecular weight of 8000 (calculated as polystyrene).

In the process of the present invention, since the condensation product does not precipitate and the condensation reaction is completed in a short reaction time irrespective of the structures of the phenol compound and the quinone diazide sulfonyl halide and a molar ratio of the quinone diazide sulfonyl halide to the phenol compound, a possibility of the industrial production of the radiation sensitive compound is increased.

The radiation sensitive compound prepared by the process of the present invention is not or hardly colored so that the positive resist composition containing such compound has a good resolution.

What is claimed is:

1. A process for preparing a radiation sensitive compound which comprises reacting a phenol compound with a quinone diazide sulfonyl halide in a mixture of a solvent having a relative dielectric constant of not larger than 10 selected from the group consisting of dioxane, tetrahydrofuran, dichloromethane and chloroform, and a solvent having a relative dielectric constant of at least 15 selected from the group consisting of methanol, ethanol, 1-propanol, 2-propanol, 1-butanol and 2-butanol, wherein the amount of the solvent having a relative dielectric constant of at least 15 is not larger than 50% by weight based on the total weight of the solvent mixture.

2. The process according to claim 1, wherein the solvent having the relative dielectric constant of not larger than 10 is dioxane.

3. The process according to claim 1 or 2, wherein the solvent having the relative dielectric constant of at least 15 is methanol.

4. The process according to claim 3, wherein an amount of methanol is not more than 1% by weight based on the whole weight of the solvent mixture.

5. The process according to claim 4, wherein an amount of methanol is not more than 0.1% by weight based on the whole weight of the solvent mixture.

6. The process for preparing a radiation sensitive compound according to claim 1, wherein the phenol compound is selected from the group consisting of 2,3,3',4-tetrahydroxybenzophenone, 2,3,4,4'-tetrahydroxybenzophenone, 2,2',4,4'-tetrahydroxybenzophenone, 2,2',3,4-tetrahydroxybenzophenone, 2,2',3,4'-tetrahydroxybenzophenone, 2,2',5,5'-tetrahydroxybenzophenone, 2,3',4',5-tetrahydroxybenzophenone, 2,3',5,5'-tetrahydroxybenzophenone, 2,2'3,4,4'-pentahydroxybenzophenone, 2,2,'3,4,5'-pentahydroxybenzophenone, 2,2',3,3',4-pentahydroxybenzophenone, 2,3,3',4,5'-pentahydroxybenzophenone, 2,3,3',4,4',5'-hexahydroxybenzophenone, 2,2',3,3'4,5'-hexahydroxybenzophenone, alkyl gallates; and oxyfravans of the formula (I):

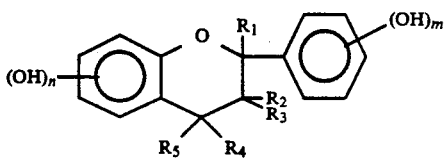

wherein n is a number of 0 to 3 and m is a number from 1 (one) to 4 provided that a sum of n and m is at least 1, $R_1$ to $R_5$ are independently a hydrogen atom, an alkyl group having preferably 1 to 4 carbon atoms, an alkenyl group having preferably 2 to 4 carbon atoms, a cycloalkyl group having preferably 5 to 7 carbon atoms or an aryl group such as a phenyl group, a naphthyl group, or a pair of $R_1$ and $R_2$ and a pair of $R_4$ and $R_5$ independently forming a ring, provided that at least one of $R_4$ and $R_5$ is an alkyl group, an alkenyl group, a cycloalkyl group or an aryl group.

7. The process for preparing a radiation sensitive compound according to claim 1, wherein the quinone diazide sulfonyl halide is selected from the group consisting of 1,2-benzoquinone diazide-4-sulfonly chloride, 1,2-naphthoquinone diazide-4-sulfonyl chloride, and 1,2-naphthoquinone diazide-5-sulfonyl chloride.

8. A process for preparing a radiation sensitive compound which comprises reacting a phenol compound with a quinone diazide sulfonyl halide in a mixture of a solvent having a relative dielectric constant of not larger than 10 and an alcohol having a relative dielectric constant of at least 15.

9. A process for preparing a radiation sensitive compound which comprises reacting a phenol compound with a quinone diazide sulfonyl halide in a mixture of dioxane having a relative dielectric constant of not larger than 10 and an alcohol having a relative dielectric constant of at least 15.

10. The process according to claims 8 or 9, wherein the amount of the alcohol is not more than 1% by weight based on the total weight of the solvent mixture.

11. The process according to claims 8 or 9, wherein the amount of the alcohol is not more than 0.1% by weight based on the total weight of the solvent mixture.

* * * * *